US012735474B2

(12) United States Patent
Huang et al.

(10) Patent No.: US 12,735,474 B2
(45) Date of Patent: Sep. 15, 2026

(54) MONOCLONAL ANTIBODY INHIBITING SMIM15 AND APPLICATION THEREOF

(71) Applicant: AFFILIATED HOSPITAL OF NANTONG UNIVERSITY, Nantong (CN)

(72) Inventors: Jianfei Huang, Nantong (CN); Bing Lu, Nantong (CN); Pingping Sun, Nantong (CN); Xiaojing Zhang, Nantong (CN)

(73) Assignee: AFFILIATED HOSPITAL OF NANTONG UNIVERSITY, Nantong (CN)

( * ) Notice: Subject to any disclaimer, the term of this patent is extended or adjusted under 35 U.S.C. 154(b) by 617 days.

(21) Appl. No.: 18/256,221

(22) PCT Filed: Jan. 4, 2022

(86) PCT No.: PCT/CN2022/070068

§ 371 (c)(1),
(2) Date: Jun. 7, 2023

(87) PCT Pub. No.: WO2022/148337

PCT Pub. Date: Jul. 14, 2022

(65) Prior Publication Data

US 2024/0018222 A1 Jan. 18, 2024

(30) Foreign Application Priority Data

Jan. 8, 2021 (CN) ......................... 202110029677.8

(51) Int. Cl.

| | |
|---|---|
| ***C07K 16/18*** | (2006.01) |
| ***G01N 33/575*** | (2026.01) |
| ***G01N 33/57515*** | (2026.01) |
| ***G01N 33/5753*** | (2026.01) |

(52) U.S. Cl.

CPC ....... *C07K 16/18* (2013.01); *G01N 33/57515* (2026.01); *G01N 33/5753* (2026.01); *G01N 33/57557* (2026.01); *C07K 2317/35* (2013.01); *C07K 2317/76* (2013.01)

(58) Field of Classification Search

CPC ................ C07K 16/18; C07K 2317/35; C07K 2317/76; G01N 33/57407; G01N 33/57415; G01N 33/57446

See application file for complete search history.

(56) References Cited

PUBLICATIONS

Cetin Z, Yakut S, Clark OA, Mihci E, Berker S, Luleci G. A 5q12.1-5q12.3 microdeletion in a case with a balanced exceptional complex chromosomal rearrangement. Gene. Mar. 1, 2013;516(1):176-80. doi: 10.1016/j.gene.2012.12.013. (Year: 2012).*

Human Protein Atlas. (n.d.-a). Expression of SMIM15 in cancer—summary—The human protein atlas. HPA. https://www.proteinatlas.org/ENSG00000188725-SMIM15/cancer (Year: 2025).*

Jallard S et al. 5q12.1 deletion: delineation of a phenotype including mental retardation and ocular defects. Am J Med Genet A. Apr. 2011;155A(4):725-31. doi: 10.1002/ajmg.a.33758. (Year: 2011).*

Rood et al. P282: Large deletion of 5q12 with dysmorphic features, poor growth, delays, behavioral anomalies, and seizures: A case report and literature review, Genetics in Medicine Open. Mar. 13, 2023; 1(1): 100310. doi:https://doi.org/10.1016/j.gimo.2023.100310 (Year: 2023).*

* cited by examiner

*Primary Examiner* — Nora M Rooney
*Assistant Examiner* — Leah Elizabeth Stein
(74) *Attorney, Agent, or Firm* — JCIPRNET

(57) ABSTRACT

A monoclonal antibody inhibiting an SMIM15 and application thereof; the antibody is secreted by a hybridoma cell strain 1M5. A preparation method includes: preparing mouse immunogen and an antigen for detection; preparing the hybridoma cell strain 1M5 against an SMIM15; screening an SMIM15 positive monoclonal antibody: identifying a subtype of the monoclonal antibody; detecting specificity of the SMIM15 positive monoclonal antibody; producing and purifying the monoclonal antibody in a BALB/c mouse; detecting purity of the antibody by SDS-PAGE; and performing function identification and application on the SMIM15 monoclonal antibody with WB, IHC and ELISA. According to the present application, the antibody secreted by the hybridoma cell strain 1M5 is an immunoglobulin, which is non-toxic, and can be used for Western blot and immunohistochemistry and used as an active ingredient to be made into a reagent or drug for diagnosis and treatment of SMIM15-related diseases.

4 Claims, 3 Drawing Sheets

Specification includes a Sequence Listing.

MONOCLONAL ANTIBODY INHIBITING SMIM15 AND APPLICATION THEREOF

REFERENCE TO A SEQUENCE LISTING

The instant application contains a Sequencing Listing which has been submitted electronically in ASCII text file and is hereby incorporated by reference in its entirety. Said TXT copy, created on Jan. 8, 2021, is named RH21035NT-seq1 and is 536 bytes in size.

TECHNICAL FIELD

The present invention belongs to the technical field of immunology and relates to a monoclonal antibody, in particular to a monoclonal antibody inhibiting an SMIM15 and application thereof.

BACKGROUND ART

Small integral membrane protein 15 (SMIM15, another name of C5orf43) is a protein coding gene, which is widely expressed in the colon, thyroid and other tissues of the body. It is known that SMIM15 includes two transcripts and 155 homologous genes. SMIM15 mainly functions to control the synthesis of protein under various physiological and pathological conditions, and further plays a key role in the processes of immune recognition between cells, material transportation, etc.

Compared with that of normal tissues, the expression quantity of SMIM15 is higher in most cancer tissues, such as glioma, gastric cancer and breast cancer, but the related mechanism and research thereof have not been reported in literature. In recent years, as immunotherapy and immune targeted therapy play an important role in the comprehensive treatment of various diseases, it is an ideal way to use antibody to direct drugs to target cells. At present, the research on protein coding gene has gradually become an important target of basic scientific research and biomedicine, which increases the market demand in biochemical reagent for medical scientific research and clinical diagnosis. As far as the reports at home and abroad are concerned, there is no monoclonal antibody with human-mouse cross reaction and high specificity inhibiting SMIM15 that can be used for the research of immunological methods.

SUMMARY

In view of the above problems existing in the prior art, the technical problem to be solved by the present invention is to provide a monoclonal antibody inhibiting an SMIM15, and another technical problem to be solved by the present invention is to provide application of the monoclonal antibody inhibiting SMIM15.

In order to solve the above technical problems, a technical solution used by the present invention is as follows:

A hybridoma cell strain 1M5 secreting the monoclonal antibody A1M5 inhibiting SMIM15 provided by the present application is preserved in China Center for Type Culture Collection on Nov. 18, 2020, with preservation number of CCTCC NO: C2020247; and the prepared monoclonal antibody inhibiting SMIM15 is named A1M5.

The monoclonal antibody A1M5 inhibiting SMIM15 is secreted by the hybridoma cell strain 1M5.

A method for producing the monoclonal antibody A1M5 by the hybridoma cell strain 1M5 is as follows:

a. In order to enhance immunogenicity, a nucleotide fragment sequence of the SMIM15 gene (Accession: NM_001048249.4) and artificial synthetic peptide fragment: CAWAEYVVEWAAKDPY (SEQ ID NO: 1) are obtained from a GenBank, and the polypeptide fragment is coupled with KLH as immunogen, named as 2019-348 polypeptide-KLH, and SPF BALB/c female mice are immunized by a conventional method;

b. spleen cells are aseptically taken from immune qualified mice as antigen sensitized B cells, the B cells are fused with myeloma cells SP2/0 in strains according to a conventional method, and then screening is performed by using a conventional HAT screening method for fused cells, so as to obtain growth clone of the fused cells;

c. monoclonal antibodies inhibiting SMIM15 positive and normal human seronegative are screened by an enzyme-linked immunosorbent assay (ELISA), 9 hybridoma cells stably secreting the monoclonal antibodies inhibiting SMIM15 are finally selected, and are named 1M4, 1M5, 1M6, 1M7, 1M8, 1M9, 1M10, 1M11 and 1M15 separately, and the monoclonal antibodies secreted by the hybridoma cells are named A1M4, A1M5, A1M6, A1M7, A1M8, A1M9, A1M10, A1M11 and A1M15 separately.

d. subtype identification is performed on the screened 9 positive cell strains, and finally 9 positive hybridoma cell strains of IgG are obtained with subtypes of G1, G2a, G2b, G2b, G2a, G2a, G2a, G2b and G2a separately;

e. Western blot (WB) is used to detect specificity of SMIM15 positive monoclonal antibodies, and results show that 2019-348 polypeptide-BSA and the SMIM15 positive monoclonal antibodies (A1M4, A1M5, A1M6, A1M7, A1M8, A1M9, A1M10, A1M11 and A1M15) may react specifically (FIG. 1);

f. the finally selected hybridoma cells 1M5 are inoculated into an abdominal cavity of an animal, and separating and purifying are performed in the animal ascites to obtain the required monoclonal antibody A1M5 inhibiting SMIM15;

g. purity of the antibody A1M5 is detected by SDS-polyacrylamide gel electrophoresis (SDS-PAGE), and results show that two clear bands appear, namely a heavy chain and a light chain separately (FIG. 2), which indicates that purification effect of the antibody is high; and h. WB performs function identification and application on the antibody inhibiting SMIM15, and finds that the antibody A1M5 has good binding activity with a natural antigen SMIM15 in gastric cancer cells, glioma cells and breast cancer cells, which indicates that the purified antibody A1M5 has good specificity and may recognize the natural antigen SMIM15 when applied in WB (FIG. 3).

i. Immunohistochemistry (IHC) is used to perform function identification on the antibody inhibiting SMIM15, and finds that the antibody A1M5 has positive staining results (FIG. 4, breast cancer; FIG. 5, glioma; FIG. 6, gastric cancer), the antibody is expressed in cytoplasm of the breast cancer, the glioma and the gastric cancer, indicating that the purified antibody A1M5 has good valence and specificity, and may be combined with tissues that overexpress SMIM15 when applied in IHC.

j. The valence of the monoclonal antibody A1M5 inhibiting SMIM15 is detected by the ELISA, it is found that concentration of the antibody A1M5 is as low as 93.75 ng/mL, the antibody has good binding activity with a polypeptide antigen (concentration is 0.0025 μg/mL) of SMIM15, and A1M5 has good ELISA reaction titer (FIG. 7).

A kit contains the monoclonal antibody A1M5 inhibiting SMIM15.

Application of the monoclonal antibody A1M5 inhibiting SMIM15 in preparing an antigen reagent for detecting the SMIM15.

Application of the monoclonal antibody A1M5 inhibiting SMIM15 in preparing therapeutic drugs, related diagnostic reagents and scientific research reagents for SMIM15-related diseases.

Beneficial effects: compared with the prior art, the present invention has the advantages:

The present invention obtains the nucleotide fragment sequence of SMIM15 gene from the GenBank (Accession: NM_001048249.4), the monoclonal antibody inhibiting SMIM15 prepared by a monoclonal antibody preparation technology is simple in preparation method and may be directly secreted by the hybridoma cell strain 1M5. The antibody is an immunoglobulin, does not harm health by means of body surface contact and a respiratory tract, and is non-toxic; and the antibody may be applied to Western blot and immunohistochemistry, and the antibody may also be potentially used as an active ingredient to be made into a reagent or drug for diagnosis and treatment of SMIM15-related diseases.

DETAILED DESCRIPTION OF THE EMBODIMENTS

Figure 1:
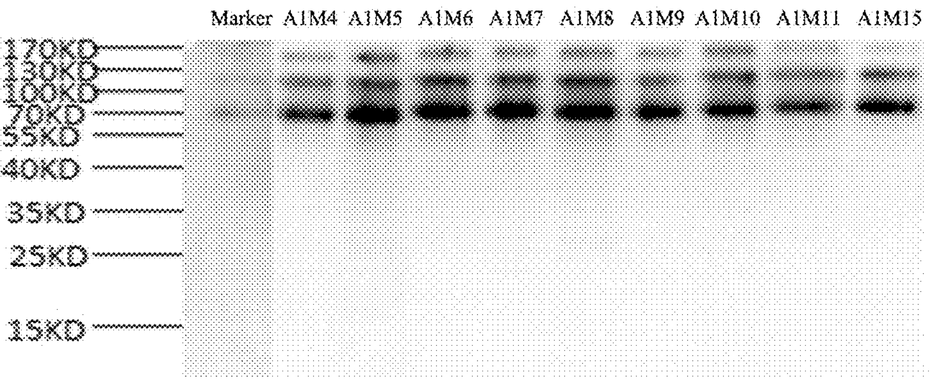
FIG. 1 shows whether 2019-348 polypeptide-BSA and SMIM15 positive monoclonal antibodies may react specifically detected by WB, and in the figure, the antibodies A1M4, A1M5, A1M6, A1M7, A1M8, A1M9, A1M10, A1M11 and A1M15 may specifically bind with SMIM15 molecules.

The present invention will be further described below with reference to specific examples. These examples are merely illustrative of the present invention and are not intended to limit the scope of the present invention. In the following examples, unless otherwise specified, the experimental methods are all conventional methods.

Example 1

Main reagents used in the following examples are:

Cell Fusion:

- IMDM medium;
- IMDM complete medium (containing 15% serum);
- 2.2% methyl cellulose (SIGMA; Item No: M0262-100G);
- A newborn calf serum; PEG1500 (Roche; Item No: 78364);
- HAT (Sigma; Item code: H0262-10VL); and
- HT (Sigma; Item code: H0137-10VL).

Monoclonal Cell Screening:

- A coating solution: sodium carbonate-sodium bicarbonate buffer solution (pH 9.6); PBS buffer solution (pH 7.4);
- A sealing solution: PBS containing 2% milk;
- Lotion: PBS-T (0.05% Tween, PBS);
- A color developing solution: 1% solution A+10% solution B (solution A: 1% TMB in DMSO; Solution B: a citrate buffer solution containing 0.1% $H_2O_2$);
- A stop solution: 2M sulfuric acid; and
- A secondary antibody: goat anti-mouse IgG/HRP.

Subtype Identification of Monoclonal Cell:

- A coated antibody (Southern Biotech);
- A sealing solution: 2% BSA+3% sucrose in PBS;
- A color developing solution: 0.2 mL of solution A+10 μL of 30% $H_2O_2$ in 10 mL of solution B (solution A: 15 mg/mL ABTS in $H_2O$; solution B: a citrate buffer solution, pH 4.0); and
- Various subtypes of secondary antibodies (Southern Biotech).

For SDS-PAGE Gel Electrophoresis and WB:

- A SDS-PAGE gel preparation kit (Beyotime biotechnology);
- 2× Loading Buffer (Beyotime biotechnology);
- A prestained protein Marker (Thermo Fisher Scientific, USA);
- Coomassie brilliant blue R-250 (Beyotime biotechnology);
- A PDVF membrane (Millipore, USA);
- Filter paper (Beyotime biotechnology);
- An IgG mouse secondary antibody (Abcam, USA); and
- An ECL developing solution (NCM Biotech).

Immunohistochemistry:

- A DAB staining solution (reinforced polymer method) kit (Fuzhou Maixin Biotech. Co., Ltd);
- A citric acid tissue antigen retrieval solution (100×) (Fuzhou Maixin Biotech. Co., Ltd);
- An endogenous peroxidase blocker (Fuzhou Maixin Biotech. Co., Ltd);
- A reaction enhancing solution (Fuzhou Maixin Biotech. Co., Ltd); and
- An enzyme labeled anti-mouse/rabbit IgG polymer (Fuzhou Maixin Biotech. Co., Ltd).

ELISA:

- An ELISA coating solution (Beijing Solarbio Science & Technology Co., Ltd);
- An ELISA stop solution (Beijing Solarbio Science & Technology Co., Ltd);
- A one-component TMB color developing solution (Beijing Solarbio Science & Technology Co., Ltd); and
- Goat anti-mouse IgG-HRP (Beijing Solarbio Science & Technology Co., Ltd).

Main Instruments Used in the Following Examples are:

a tissue Chip system (UT06, Korea, Unitma Co., Ltd.); an inverted microscope (DMIRB, Germany, Leica Camera); a full automatic microplate reader (SN209941, USA, US Bio-Tek); a carbon dioxide water jacket incubator (HEPACLASS 100, USA, Thermo Fisher Scientific); a pH meter (EL20, Switzerland, Mettler Toledo); a vertical electrophoretic transfer system (1658033, USA, BIO-RAD); and a UVP gel imaging system (UVP Biosp, USA, UVP).

Example 1

1. Preparation of Mouse Immunogen and an Antigen for Detection

Polypeptide design and synthesis 2019-348 polypeptide: CAWAEYVVEWAAKDPY-NH2 (sequence) (SEQ ID NO: 1), polypeptide coupling: polypeptide coupled with KLH was quantified at 3.0 mg/mL (name: 2019-348 polypeptide-KLH).

2. Preparation of a Hybridoma Cell Inhibiting SMIM15

4 female SPF BALB/c female mice were immunized subcutaneously with "2019-348 polypeptide-KLH" at amount of 60 μg of protein per mouse for the first time, and numbered as 1, 2, 3 and 4. The mice were subjected to subcutaneous booster immunization for the first time, and immunization amount was 30 μg of protein per mouse. Subsequently, booster immunization was performed for the second time, the third time, the fourth time and the fifth time separately, and the immunization amount was 30 μg of protein per mouse. Blood was taken from eye sockets, and valence of a serum was detected. The mice were intraperitoneally impacted with 50 μg of immunogen.

Immunizing Potency Detection Steps:

2 μg/mL of "2019-348 polypeptide-BSA" was coated overnight at 4° C.; 2% skimmed milk powder was sealed at 37° C. for 2 h; the serum was diluted by 2 times from 200 times in gradient, blank control was PBS, and negative control was a negative serum diluted by 200 times; and the mice were impacted to do a cell fusion experiment; and Spleen cells of the mice and SP2/0 cells (myeloma cells) were fused by a PEG method, and fused cells were screened and cultured in a semi-solid culture medium (containing HAT).

Cell Fusion Steps:

a. SP2/0 cells in a good condition were gently blown off a culture bottle wall and sucked into a centrifuge tube having a capacity of 50 mL;

b. eyeballs of the mice were taken for blood, then the mice were put to death by pulling necks, and put in alcohol having a concentration of 75% for 5 min;

c. a small amount of serum-free IMDM was poured into a plate, and cells were sieved into an inner core of a syringe to be put into the plate; spleens of the mice were removed with scissors and tweezers to be put on a cell sieve; the spleens were gently crushed with the inner core of the syringe, the crushed cells were sucked into the centrifuge tube with the SP2/0, and centrifuged at 1500 rad/min for 5 min;

d. thymuses of the mice were removed with the scissors and the tweezers to be crushed; crushed thymocytes were sucked into a centrifuge tube having a capacity of 15 mL, then 1 mL of HAT was added, and the centrifuge tube was put in an incubator for later use;

e. supernatant was removed from the centrifuged cells, the cells were gently blown with the serum-free IMDM, and centrifugation was performed (1500 rad/min, 5 min);

f. the centrifuged cell supernatant was poured, the cells suspended at a bottom of the centrifuge tube were patted, the centrifuge tube was put in warm water at 37° C., 1 mL of PEG (Roche) was slowly added in warm water in 1 min for standing for 1 min, then 2 mL of the serum-free IMDM was slowly added, then 8 mL of the serum-free IMDM was slowly added within 2 min, and centrifugation was performed at 1000 rad/min for 5 min; and g. a supernatant was poured, 10 mL of serum was added, the cells were carefully blown evenly, and the prepared thymocytes were poured; then 25 mL of sterilized semi-solid culture medium was added, and thorough mixing was performed; then a mixture was evenly poured into 30 cell culture dishes; and the cell culture dishes were put in a wet box, and then the wet box was put into the incubator for culture.

3. Screening of a Positive Monoclonal Antibody Inhibiting SMIM15

2 weeks later, 10 plates×93 cells were selected for monoclone and cultured in 96-hole cell culture plates (the plates were covered with the thymocytes in advance, with 100 μL/hole); and 3 days later, the plates were coated with "2019-348 polypeptide-BSA", the selected clones was screened for the first time by an ELISA method, and 15 positive hybridoma cell strains were obtained, the numbers of the strains were 1M1, 1M2, 1M3, 1M4, 1M5, 1M6, 1M7, 1M8, 1M9, 1M10, 1M11, 1M12, 1M13, 1M14 and 1M15.

Experimental Steps:

a. "2019-348 Polypeptide-BSA" was diluted with the coating solution (sodium carbonate-sodium bicarbonate buffer solution, pH9.6) to a final concentration of 2 μg/mL, with 100 μL/hole, and stays overnight at 4° C.; and then "2019-348 Polypeptide-BSA" was washed with PBST (PBS containing 0.05% Tween) for 3 times;

b. sealing solution (PBS containing 2% milk) was used for sealing, with 200 μL/hole, in the incubator at 37° C. for 2 h, and washing was performed with PBST for 3 times;

c. a primary antibody (a cell culture supernatant), negative control (a SP2/0 culture supernatant), blank control (PBS) and positive control (a positive serum, diluted by 1000 times) were added, all of which were 100 μL/hole, in the incubator at 37° C. for 1 h; and washing was performed with PBST for 3 times;

d. the secondary antibody diluted by 20000 times by the PBS was added, with 100 μL/hole, and incubated at 37° C. for 1 h; and the secondary antibody was taken out then washed with the PBST for 3 times;

e. color development was performed, 100 μL of color developing solution was added to each hole for color development for 5 min;

f. 50 μL of stop solution was added to each hole to stop; and g. a light absorption value was measured at double wavelengths (450, 630), and the hybridoma cell strains that were positive for immune protein screening were in a total of 15 strains.

15 positive cell strains were coated with "2019-348 polypeptide-BSA" and screened for the second time by ELISA, finally, 9 hybridoma cells secreting antibodies inhibiting SMIM15 were selected and named as 1M4, 1M5, 1M6, 1M7, 1M8, 1M9, 1M10, 1M11 and 1M15 separately, and monoclonal antibodies secreted by which were named as A1M4, A1M5, A1M6, A1M7, A1M8, A1M9, A1M10, A1M11 and A1M15 separately.

4. Subtype Identification of Monoclonal Cell

Subtype identification was performed on the screened 9 positive cell strains, and finally 9 positive hybridoma cell strains of IgG were obtained with subtypes of G1, G2a, G2b, G2b, G2a, G2a, G2a, G2b and G2a separately.

Experimental Steps:

a. the coated antibody (Southern Biotechnology) was diluted with 100 mM PBS (pH 7.4) to 0.5 μg/ml, 0.1 ml of PBS was added to each hole, and stay overnight at 4° C.;
b. the antibody was washed with the PBST twice, 200 μL of sealing solution was added to each hole, and incubated at 37° C. for 2 h;
c. the antibody was washed with the PBST for three times, 100 μL of hybridoma supernatant was added to each hole, and incubated at 37° C. for 1 h;
d. the antibody was washed with the PBST for three times, 0.1 mL of HRP-labeled antibody diluted with the blocking solution at a ratio of 1:10000 (κ, λ) or 1:20000 (others) was added into appropriate holes separately, and incubated at 37° C. for 1 h; and
e. the antibody was washed with the PBST for three times, 50 μL of substrate solution was added to each hole, and the light absorption value was measured at dual wavelengths (450, 630) within 10-20 min, and finally, subtypes of 9 positive monoclonal cell strains were obtained, namely G1, G2a, G2b, G2b, G2a, G2a, G2a, G2b and G2a separately.

5. Specific Detection of Monoclonal Antibodies a. a protein vertical electrophoresis tank was mounted as specified;
b. separation gel having a concentration of 12% was prepared: gel stands at room temperature for 50 min until gel was polymerized;
c. spacer gel was prepared: the spacer gel having a concentration of 5% was prepared after the separation gel was completely polymerized;
d. sample loading was performed: after the spacer gel was completely polymerized, a comb was pulled out, SDS glycine electrophoresis buffer was added, a sample loading hole was cleaned, and the prepared sample (2019-348 polypeptide-BSA) was added into the sample loading hole;
e. electrophoresis was performed: a power supply was powered on, constant voltage current of 80 V was used for 50 min, then constant voltage current was converted to constant voltage current of 120V for continuous electrophoresis about 40 min after the protein prestained Marker was separated;
f. film transfer was performed: film transfer was performed for 90 min at 300 mA current;
g. the primary antibodies: after membrane transfer was completed, the blocking solution was used for blocking for 2 h, and then the diluted primary antibodies (the monoclonal antibodies secreted by the 9 hybridoma cells) were given;
h. secondary antibody: the secondary antibody of HRP-labeled goat anti-mouse IgG was prepared according to a dilution ratio of 1:5000 and incubated at room temperature for 2 hours; and
i. developing was performed: developing was performed with the UVP gel imaging system, and photos were taken for preservation.

Results show that the monoclonal antibody inhibiting SMIM15 may specifically bind to the coupled polypeptide of SMIM15 (2019-348 polypeptide-BSA) to form a positive band. The results show that positive supernatants secreted by the 9 hybridoma cell strains have good specificity for recognizing SMIM15 molecules (FIG. 1).

6. Production and Purification of Monoclonal Antibodies in BALB/c Mice

Six-week-old mice were inoculated with 0.5 mL of pristane, 10 days later, 1M5 and a 1M15 cell suspension diluted with an RPMI-1640 basal culture medium were intraperitoneally inoculated into the mice, further, myeloma cell SP2/0 was used as a control group, and each mouse was inoculated with $5\times10^6$ cells; and 10 days later, the ascites was collected, and centrifuged, a supernatant was taken, impurities were removed by silica powder, then the antibodies were purified by a Protein G affinity chromatography column (Amersham), and after purification, the antibodies were subpackaged and frozen at −80° C.

7. Detection of Purity of Monoclonal Antibody Inhibiting SMIM15 with SDS-PAGE a. the protein vertical electrophoresis tank was mounted as specified;
b. the separation gel having a concentration of 12% was prepared: the gel stands at room temperature for 50 min until the gel was polymerized;
c. the spacer gel was prepared: the spacer gel having a concentration of 5% was prepared after the separation gel was completely polymerized;
d. sample loading was performed: after the spacer gel was completely polymerized, the comb was pulled out, the SDS glycine electrophoresis buffer was added, the sample loading hole was cleaned, and the prepared sample (purified antibody) was added into the sample loading hole;
e. electrophoresis was performed: the power supply was powered on, constant voltage current of 80 V was used for 50 min, then constant voltage current was converted to constant voltage current of 120V for continuous electrophoresis about 40 min after the protein prestained Marker was separated; and
f. after electrophoresis, the power supply was turned off to take out the gel, the gel was strained gently with the Coomassie Brilliant Blue R-250 dye solution for 4 h at room temperature, then protein bands were observed after fully decoloring of a decoloring solution, and photos were taken.

Figure 2:
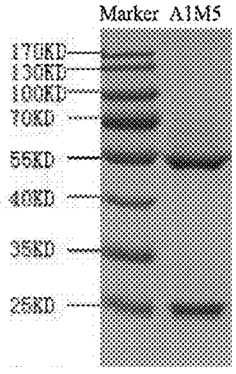
FIG. 2 shows purity of the monoclonal antibody A1M5 inhibiting SMIM15 detected by SDS-PAGE, and in the figure, two clear bands occur: namely a heavy chain (55KD) and a light chain (25KD) separately.

Results show that the monoclonal antibody A1M5 inhibiting SMIM15 shows the two clear bands by SDS-PAGE electrophoresis, namely, the heavy chain and the light chain separately, indicating that the purified antibody has high purification effect (FIG. 2).

8. Function Identification and Application of Antibody Inhibiting SMIM15 by WB a. Gastric cancer cells (MKN-1), glioma cells (U87-mg) and breast cancer cells (MCF-7) with the number of $1\times10^7$ were lysed in RIPA lysate separately to obtain total cell proteins.
b. Gel electrophoresis and membrane transfer were performed as described above, and the primary antibody was diluted A1M5 (1:500), the secondary antibody was HRP-labeled goat anti-mouse IgG (1:5000), and then the primary antibody and the secondary antibody were developed and preserved.

Figure 3:
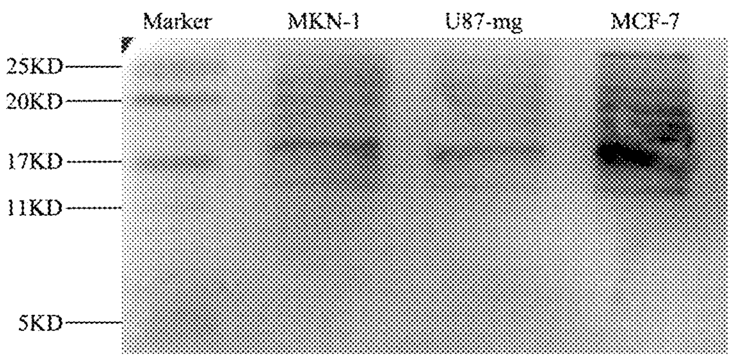
FIG. 3 is a result of a reaction between the monoclonal antibody A1M5 inhibiting SMIM15 and a natural antigen from cells detected by WB, in the figure, a clear band appears, and A1M5 has good binding activity with the natural antigen SMIM15.

Results show that A1M5 has good binding activity with the natural antigen SMIM15 in various tumor cells, and may recognize SMIM15 natural antigen in WB application (FIG. 3).

9. Function Identification and Application of Antibody Inhibiting SMIM15 by IHC a. sections (breast cancer, glioma and gastric cancer slices) were baked in an oven at 70° C. for 90 min, baked at 60° C. for 60 min, then dewaxed with xylene twice, with each time for 5 min, and pass through alcohol having concentrations of 100%, 95% and 70% in turn after dewaxing, with each time for 5 min;

b. antigen restoration was performed in a microwave oven, with 100% power for 2.5 min, and 20% power for 15 min, and then the antigen was washed with PBS after cooling;

c. the antigen was incubated with hydrogen peroxide having a concentration of 3% for 30 min and washed with PBST for 2 min and 3 times;

d. the antigen was seals with the PBS solution containing 5% BSA for 30 min;

e. the primary antibody (purified antibody) was incubated at 4° C. overnight;

f. a tissue chip was taken out at 4° C. and left at room temperature for half an hour, then washed with PBST for 2 min and 3 times;

g. a second antibody enhancement solution was added, incubated at room temperature for 20 minutes, and washed with PBST for 2 min and 3 times;

h. the second antibody was added, and washed with PBST for 2 min and 3 times after room temperature for 30 min;

i. color was developed with DAB, and color developing was stopped immediately after color was developed completely;

j. the second antibody was put into hematoxylin for 30 seconds, differentiated with hydrochloric acid and alcohol, and then washed with running water for 10 min; and k. the alcohol having concentrations of 70%, 95% and 100% were put in turn for 5 min each time, pass through xylene twice for 5 min each time, finally air dried naturally, and sealed with neutral balsam.

Figure 4:
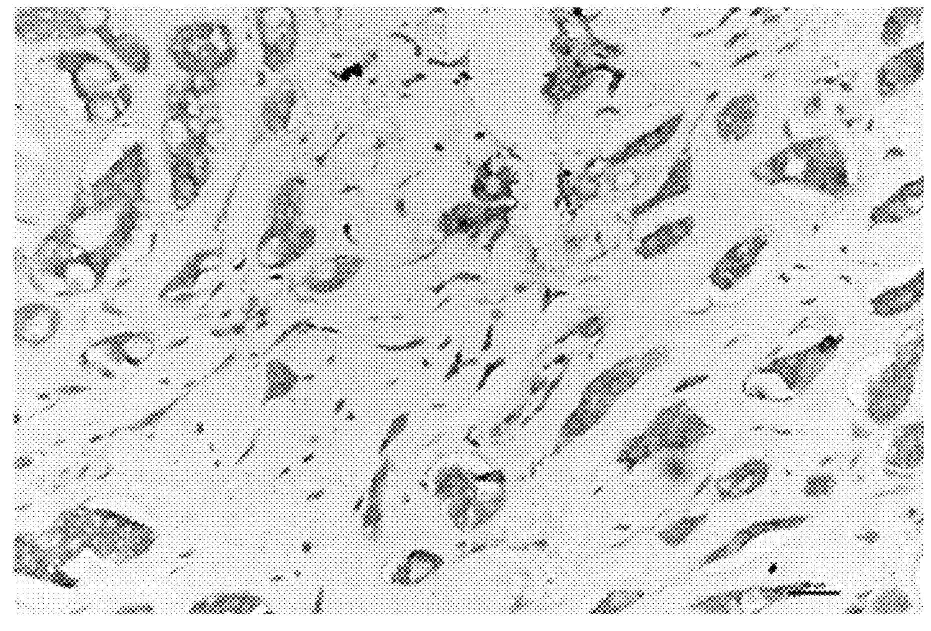
FIG. 4 is a diagram of expression of the monoclonal antibody A1M5 inhibiting SMIM15 in breast cancer tissues detected by IHC, and in the figure, cytoplasm in breast cancer cells is positively located.
Figure 5:
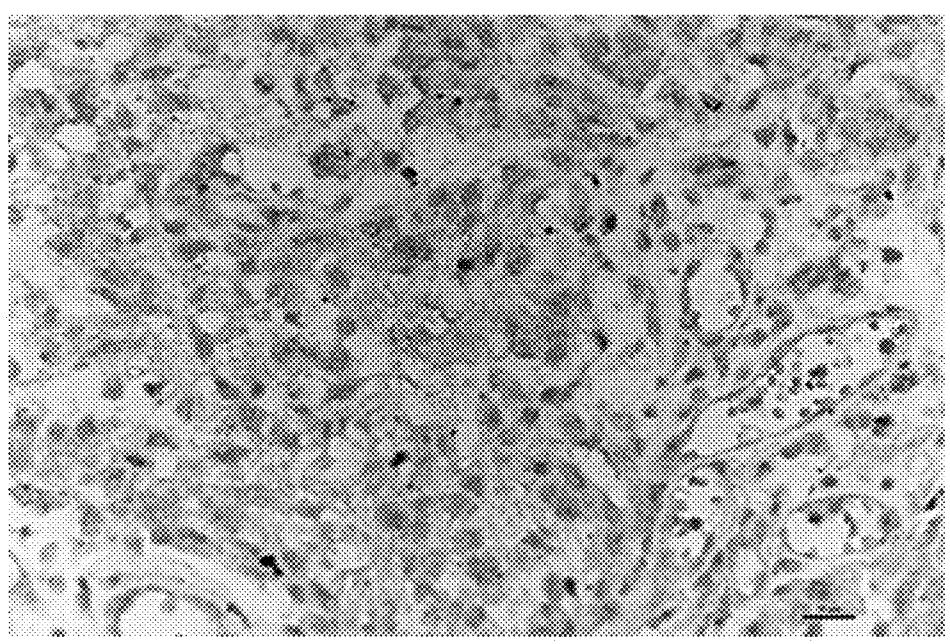
FIG. 5 is a diagram of expression of the monoclonal antibody A1M5 inhibiting SMIM15 in glioma tissues detected by IHC, and in the figure, cytoplasm in glioma cells is positively located.
Figure 6:
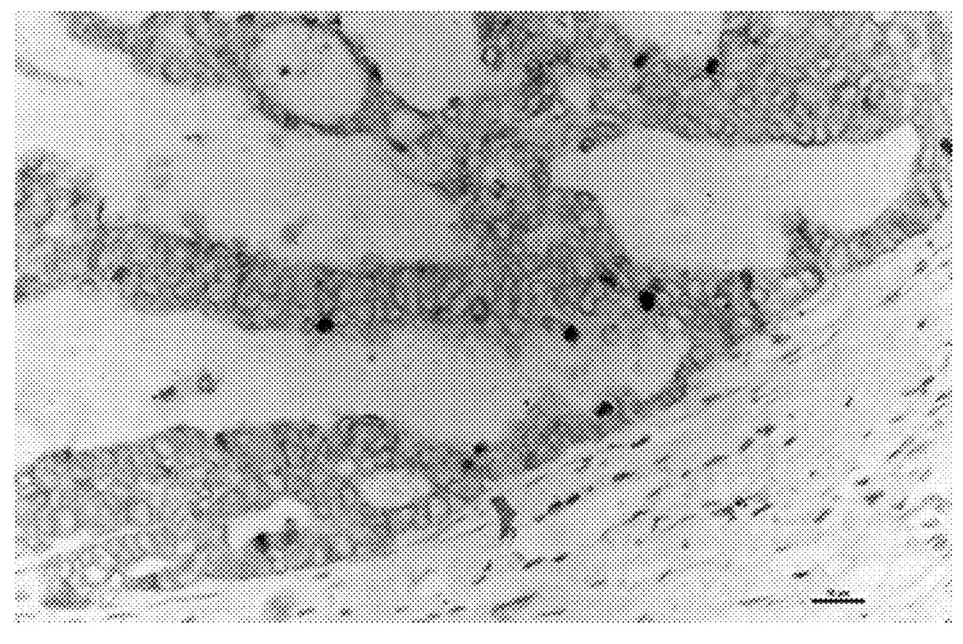
FIG. 6 is a diagram of expression of the monoclonal antibody A1M5 inhibiting SMIM15 in gastric cancer tissues detected by IHC, and in the figure, cytoplasm in gastric cancer cells is positively located.

Straining results show that the antibody A1M5 has the positive staining results (FIG. 4, the breast cancer; FIG. 5, the glioma; FIG. 6, the gastric cancer), the antibody was expressed in the cytoplasm of the breast cancer, the glioma and the gastric cancer, indicating that the purified antibody A1M5 has good valence and specificity, and may be combined with the tissues that overexpress SMIM15 when applied in IHC.

10. Detection of Valence of Monoclonal Antibody A1M5 Inhibiting SMIM15 with ELISA a. the coupled polypeptide of SMIM15 (2019-348-BSA) was diluted with the coating solution (sodium carbonate-sodium bicarbonate buffer solution, pH9.6) to final concentrations of 0.01 μg/mL, 0.005 μg/mL and 0.0025 μg/mL separately, with 100 μL/hole, and stays overnight at 4° C.; and then the coupled polypeptide was washed with PBST (PBS containing 0.05% Tween) for 3 times;

b. the sealing solution (PBS containing 2% milk) was used for sealing, with 200 μL/hole, in the incubator at 37° C. for 2 h, and washing was performed with PBST for 3 times;

c. the purified antibody A1M5 with different concentrations (initial concentration was 1.2 mg/mL, diluted at 1:200, 1:400, 1:800, 1:1600, 1:3200, 1:6400, 1:12800 separately in gradient, and the negative control was PBS), with 100 μL/hole, and incubated at 37° C. for 1 h; and the purified antibody A1M5 was washed with PBST for 3 times;

d. the secondary antibody (goat anti-mouse IgG/HRP Southern Biotech) diluted by 3000 times by the PBS was added, with 100 μL/hole, and incubated at 37° C. for 1 h; and the secondary antibody was taken out then washed with the PBST for 3 times;

e. color development was performed, the color developing solution was added with 100 μL/hole for color development for 10 min;

f. 50 μL of stop solution (2M sulfuric acid) was added to each hole to stop; and g. the light absorption value was measured at double wavelengths (450, 630).

Figure 7:
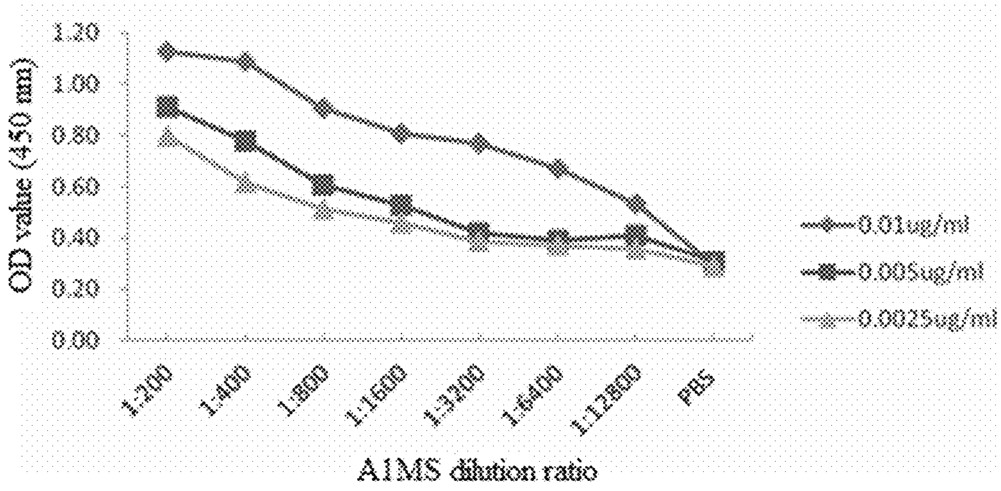
FIG. 7 shows reaction valence of the monoclonal antibody A1M5 inhibiting SMIM15 and SMIM15 coupled polypeptide detected by ELISA, which shows the antibody A1M5 has a high titer reaction.

Experimental results of indirect ELISA show that the concentration of the antibody A1M5 was as low as 93.75 ng/mL, the antibody has good binding activity with the polypeptide antigen (concentration was 0.0025 μg/mL) of SMIM15, and A1M5 has good ELISA reaction titer (FIG. 7).

To sum up, the obtained monoclonal antibody A1M5 was a monoclonal antibody inhibiting SMIM15 and has high specificity for recognizing the SMIM15 protein antigen, which may be used in the immunological research of IHC and potentially used in the diagnosis and treatment of SMIM15-related diseases.

What is claimed is:

1. A monoclonal antibody A1M5 secreted by a hybridoma cell strain 1M5 with deposit number CCTCC NO: C2020247 wherein the monoclonal antibody A1M5 inhibits small integral membrane protein 15 (SMIM15).

2. A method for producing the monoclonal antibody A1M5 of claim 1, comprising: immunizing mice with an antigen, wherein the antigen is SEQ ID NO:1 coupled with KLH.

3. A kit comprising the monoclonal antibody A1M5 of claim 1.

4. A hybridoma cell strain secreting a monoclonal antibody A1M5 wherein the hybridoma cell strain is 1M5 with deposit number CCTCC NO: C2020247.

* * * * *

SEQUENCE LISTING

```
<160> NUMBER OF SEQ ID NOS: 1

<210> SEQ ID NO 1
<211> LENGTH: 16
<212> TYPE: PRT
<213> ORGANISM: Artificial Sequence
<220> FEATURE:
<223> OTHER INFORMATION: It is synthesized.

<400> SEQUENCE: 1

Cys Ala Trp Ala Glu Tyr Val Val Glu Trp Ala Ala Lys Asp Pro Tyr
1               5                   10                  15
```